US006971878B2

(12) United States Patent  (10) Patent No.: US 6,971,878 B2
Pond  (45) Date of Patent: Dec. 6, 2005

(54) APPARATUS AND METHODS FOR TREATING TOOTH ROOT CANALS

(76) Inventor: Gary J. Pond, 2816 N. Main St., Racine, WI (US) 53402

( * ) Notice: Subject to any disclaimer, the term of this patent is extended or adjusted under 35 U.S.C. 154(b) by 0 days.

(21) Appl. No.: 10/770,356

(22) Filed: Feb. 2, 2004

(65) Prior Publication Data

US 2005/0170312 A1     Aug. 4, 2005

(51) Int. Cl.[7] ................................................ A61C 5/02
(52) U.S. Cl. ........................................................ 433/81
(58) Field of Search .......................................... 433/81

(56) References Cited

U.S. PATENT DOCUMENTS

| | | |
|---|---|---|
| 3,919,775 A | 11/1975 | Malmin |
| 4,021,921 A | 5/1977 | Detaille |
| 4,247,288 A | 1/1981 | Yoshii et al. |
| 4,993,947 A | 2/1991 | Grosrey |
| 5,295,828 A | 3/1994 | Grosrey |
| 2002/0072032 A1 * | 6/2002 | Senn et al. .................. 433/80 |

* cited by examiner

Primary Examiner—Cary E. O'Connor
(74) Attorney, Agent, or Firm—Ryan Kromholz & Manion, S.C.

(57) ABSTRACT

Systems and methods provide for automated, cyclic delivery and evacuation of a treatment or irrigation solution from a tooth root pulp chamber and pulp canals. A manifold has a base member sized and configured to rest on a crown of an instrumented tooth and a top member sized and configured to couple with the base member to define an inlet chamber and an outlet chamber. The distal end of a needle is passed through an opening between the inlet and outlet chambers and extended distally beyond the base member into a pulp canal. The proximal end of the needle includes an opening in fluid communication with the inlet chamber. A solution is transferred from a fluid supply source to the inlet chamber and through the needle into the pulp chamber and pulp canals. The spent solution is evacuated from the pulp chamber and pulp canals through the outlet chamber.

16 Claims, 11 Drawing Sheets

APPARATUS AND METHODS FOR TREATING TOOTH ROOT CANALS

FIELD OF THE INVENTION

The invention relates to devices and methods for the treatment and irrigation of dental pulp chambers and pulp canals.

BACKGROUND OF THE INVENTION

Endodontic or root canal therapy is a common procedure in which a dentist or endodontist removes the nerve and dental pulp from a tooth in cases where the nerve has been damaged by a cavity, trauma (e.g., fracture of the tooth), disease (e.g., infection), or other reasons. This procedure not only allows the individual to keep a tooth that otherwise could have had to be removed, but relieves the individual of pain and discomfort.

The treatment typically requires the removal of the pulp tissue from the canal(s). The pulp chamber and root canal(s) of the tooth are then cleaned. Finally, the pulp chamber is shaped and sealed.

The tooth to be treated is either living, and its canals contain a vasculo-nervous bundle, or is dead and its canals then contain a necrotic magma. The pulp canals present the most difficult portion of the tooth to be cleaned. A tooth can be mono- or pluri-rooted, increasing the complexity of the tooth treatment.

Conventional techniques for treating the pulp canals consists of using hand held rods fitted with metal bristles, in the form of rasps or files in a variety of gauges. These techniques require manually removing the vasculo-nervous bundle or the necrotic magma.

These conventional manual techniques present numerous disadvantages. Inherent with the positioning of teeth inside a patients mouth, space is limited to perform this intricate work. In addition, the pulp canals can be extremely fine and can also be of an irregular form. This requires the instruments to be small and delicate, presenting the problem of the instruments breaking within the pulp canal, which may necessitate complete removal of the tooth. In some cases the pulp canal is so fine that mechanical treatment is precluded.

To overcome the problems inherent in mechanical procedures, a variety of biochemical treatments have been employed to chemically attack and decompose the nervous bundle or necrotic magma. For example, ethylene diamine tetracetic acid (EDTA) is commonly employed as a treatment solution that is introduced into the pulp chamber and pulp canals to chemically treat dental roots.

It is important to the successful outcome of the procedure that the pulp chamber and pulp canals be sufficiently cleaned after the vasculo-nervous bundle or the necrotic magma has been removed. The cleaning reduces bacteria and other debris that could result in infection or abscess or otherwise result in a less than satisfactory outcome. The pulp chamber and pulp canals are cleaned with an irrigation solution, e.g., a NaOCl solution or antiseptic solution, to prepare the tooth for sealing.

A variety of techniques are employed to introduce treatment and irrigation solutions into the dental root. The instrumented tooth opening may be flushed using a hand held irrigation device. Manual treatment and irrigation of the dental root is a tedious and time-consuming task. In addition, manual methods may not consistently fill and drain the entire pulp chamber and pulp canals, resulting in less than satisfactory preparation of the tooth.

Mechanical, automated systems for introducing treatment and irrigation solutions into the dental pulp chamber and pulp canals are known. One common system employs a tooth manifold for placement on an instrumented tooth. Such systems are described in U.S. Pat. Nos. 4,021,921 and 4,993,947. The manifold has an inlet chamber for delivery of a solution and an evacuation chamber for draining of the solution. The solution is delivered via the inlet chamber into the pulp chamber, from which it flows into the pulp canals. The pulp chamber and pulp canals define a fluid reservoir. One inherent problem with such systems is delivering the solution to the bottom of the fluid reservoir with sufficient pressure to consistently dislodge debris deep within the pulp canal.

The need remains for treatment systems that deliver a treatment or irrigation solution directly into the deepest portions of the pulp canals and thoroughly evacuate the spent fluid. The need further remains for treatment systems that provide ease and convenience of use for the dental practitioner and that are time-efficient and minimize patient discomfort.

SUMMARY OF THE INVENTION

According to one aspect of the invention, a tooth root canal treatment system comprises a manifold having a base member sized and configured to rest on a crown of a tooth and a top member sized and configured to couple with the base member. The base and top members together define an inlet chamber and an outlet chamber. A fluid supply source is coupled to the inlet chamber. A draining mechanism is coupled to the outlet chamber. Means are provided for preventing fluid communication between the inlet chamber and the outlet chamber.

The distal end of a needle is sized and configured for passage through an opening between the inlet and outlet chambers to extend distally beyond the base member. The distal end of the needle is in fluid communication with the outlet chamber. The proximal end of the needle includes an opening in fluid communication with the inlet chamber.

In one embodiment, the needle includes a flexible shaft. In one embodiment, the opening between the top and base members is a perforation. In an alternative embodiment, the opening between the top and base members is a valve, e.g., a duck bill valve.

The fluid delivered may be a treatment solution, e.g., sodium hypochlorite. The fluid may also be an irrigation solution, e.g., water.

According to another aspect of the invention, a method of treating a tooth root canal provides a needle having a proximal end and a distal end. The dental practitioner places a base on a crown of an instrumented tooth. The distal end of the needle is passed through an opening in the base and into a pulp chamber and a pulp canal of the tooth. A cap is placed on the base to form a tooth manifold having an inlet chamber and an outlet chamber. The proximal end of the needle communicates with the inlet chamber and the distal end of the needle communicates with the outlet chamber. The inlet chamber is coupled to a fluid source and the outlet chamber is coupled to a draining mechanism. Fluid is drawn through the inlet chamber into the pulp chamber and pulp canal. Spent fluid is evacuated from the pulp chamber and the pulp canal through the outlet chamber.

Another aspect of the invention provides an automated system for treating a tooth root canal having a pulp chamber and pulp canal defining a fluid reservoir. The system comprises a tooth manifold having an inlet chamber and an outlet chamber. The inlet chamber is coupleable to a fluid supply source and the outlet chamber is coupleable to an evacuation source. Means are provided for directing fluid from the inlet chamber to the bottom of the fluid reservoir and for evacuating the fluid through the evacuation chamber from the fluid reservoir.

DESCRIPTION OF THE PREFERRED EMBODIMENT

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention, which is defined by the claims.

I. Tooth Manifold

Figure 1:
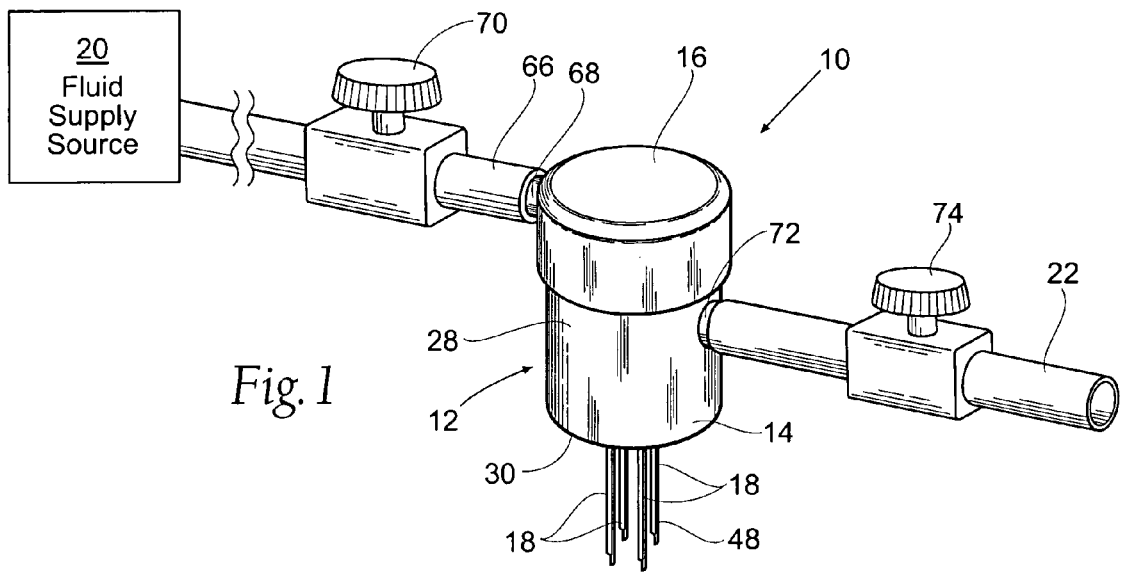
FIG. 1 is a perspective view of a system for treating tooth root canals.

FIG. 1 shows a system 10 for delivery and evacuation of a material to a pulp chamber and pulp canals deep within a tooth root during endodontic or root canal therapy. The system 10 includes a tooth manifold 12 having a bottom or base member 14 and a cap 16. The manifold 12 supports an irrigation needle 18 that permits fluid flow through the manifold 12, as will be described in detail later. The manifold 12 is coupleable to a fluid supply source 20 and evacuation tubing 22 to control and regulate delivery of fluid and evacuation of spent fluid, as will also be described in greater detail later. The fluid delivered may be a treatment solution, e.g., Dakin's solution, which chemically dissolves organic debris. The fluid delivered can also be an irrigation solution, e.g., water or antiseptic solution, which washes the debris away. The pulp chamber and pulp canals define a fluid reservoir for receiving and holding the solution. The system 10 provides consistent and thorough fill and evacuation of the fluid reservoir during each cycle, including fill and removal deep within pulp canal.

The system 10 provides for automated cyclic filling of the pulp chamber and pulp canals with a solution and evacuation of the solution from the pulp chamber and pulp canals. The system 10 can be used throughout the multiple phases of the endodontic treatment process. For example, the system 10 can be used to first prepare the tooth by delivering a treatment solution, and subsequently to irrigate the tooth by delivering an irrigation solution.

Further, the system 10 allows the dental practitioner to treat more than one tooth simultaneously. The practitioner simply employs a separate manifold for each instrumented tooth.

The practitioner is able to control the treatment process externally to the mouth of the patient. Once in place, the system 10 requires no or minimal hands-on time, freeing the practitioner, at least temporarily, for other tasks. The automated nature of the system 10 provides generally consistent delivery and evacuation cycles, thereby assuring sufficient filling and evacuation of the fluid reservoir in each cycle and in a time-efficient manner.

With reference now to FIGS. 2–5, the base member 14 is cup-shaped or otherwise sized and configured to be placed on and rest on the crown 24 of an instrumented tooth 26. The base 14 includes a flexible skirt portion 28 having an open bottom 30 permitting the base 14 to rest on the crown 24 of the tooth 26 in a snug fit engagement to close the pulp chamber 32 and pulp canals 34 and vacuum seal the tooth 26. To further secure the base 14 on the tooth 26, an attachment compound 33 may be placed around the crown 24 of the tooth 26 prior to placing the base 14 on the tooth 26 (see FIG. 4). The attachment compound 33 may be ZAP IT® cyanoacrylate ester, latex, epoxy, or other suitable biocompatible compound.

The overall configuration of the base 14 allows for placement of the base 14 over a single tooth 26 with the ability to seal the tooth 26 and prevent associated solution (S) from escaping into the patient's mouth. The open bottom configuration also provides communication between the fluid reservoir (i.e., the pulp chamber 32 and pulp canals 34) and the manifold.

The base 14 can be made of any suitable biocompatible material, e.g., silicon.

The base 14 includes an interior recess 36 for receiving a perforated screen 38. The screen 38 includes a plurality of openings 40 and is sized and configured to rest on the recess 36 within the base 14. An annular ridge 42 extends from a lip 44 around the circumferential margin of the base 14 above the screen 38 to mate with the cap 16 (see also FIG. 1).

Figure 5:
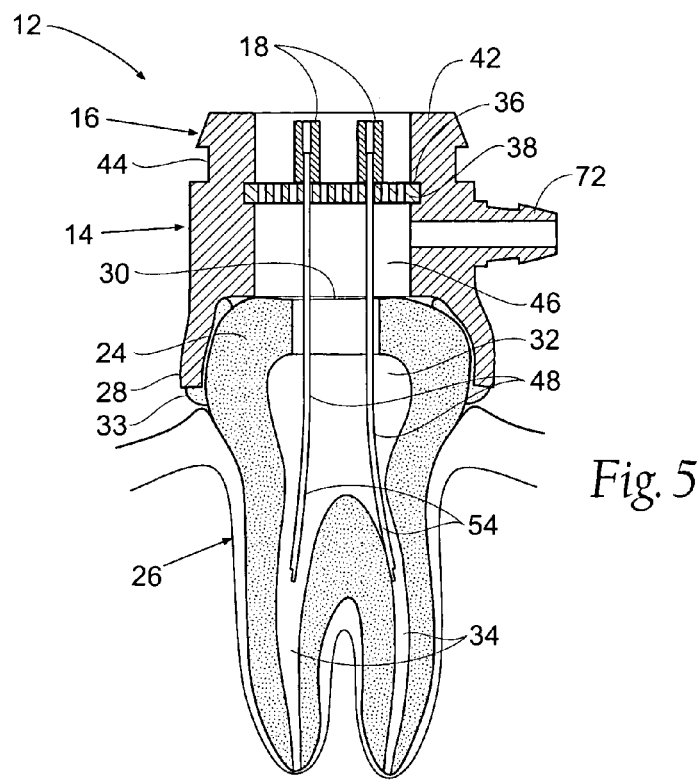
FIG. 5 is a side sectional view of the base and needles in place within an instrumented tooth, illustrating placement of the distal end of the needles deep within the pulp chambers.

As illustrated in FIG. 5, the area of the base 14 between the crown 24 of the tooth 26 and the screen 38 defines an outlet or evacuation chamber 46. The evacuation chamber 46 is in fluid communication with the pulp chamber 32 and pulp canals 34 through open bottom 30.

As FIG. 5 also illustrates, the screen 38 allows selective placement of the flexible irrigation needle 18 within an instrumented pulp canal 34. It is contemplated that the number and configuration of the openings 40 can vary to allow the desired placement of the needle 18 within a specific pulp canal 34 (see also FIG. 2). The screen 38 can be made of any suitable biocompatible material.

Figure 2:
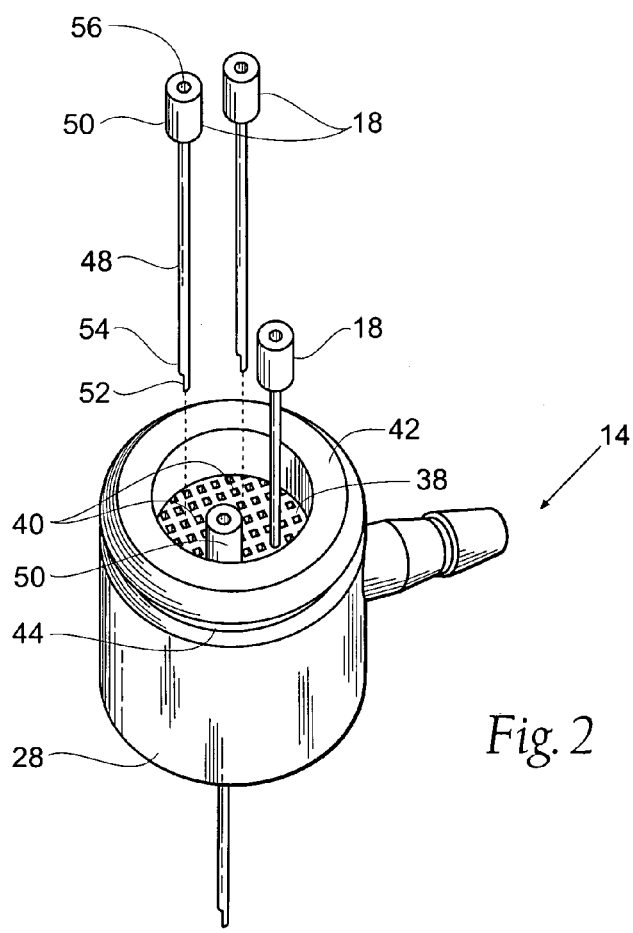
FIG. 2 is a partially exploded perspective view of the base of the system shown in FIG. 1, illustrating placement of needles through perforations in a screen within the base.
Figure 3:
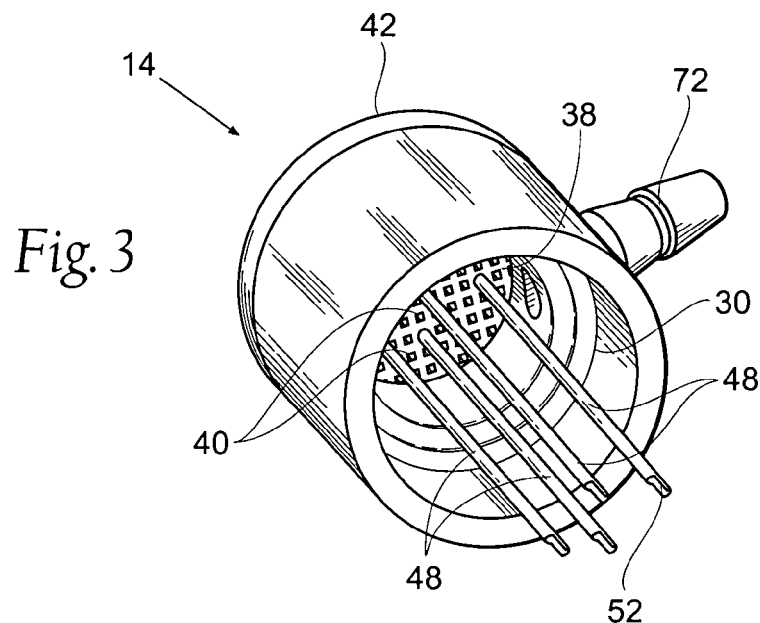
FIG. 3 is a bottom perspective view of the base shown in FIG. 2, illustrating the distal end of the needles extending beyond the distal end of the base.
Figure 4:
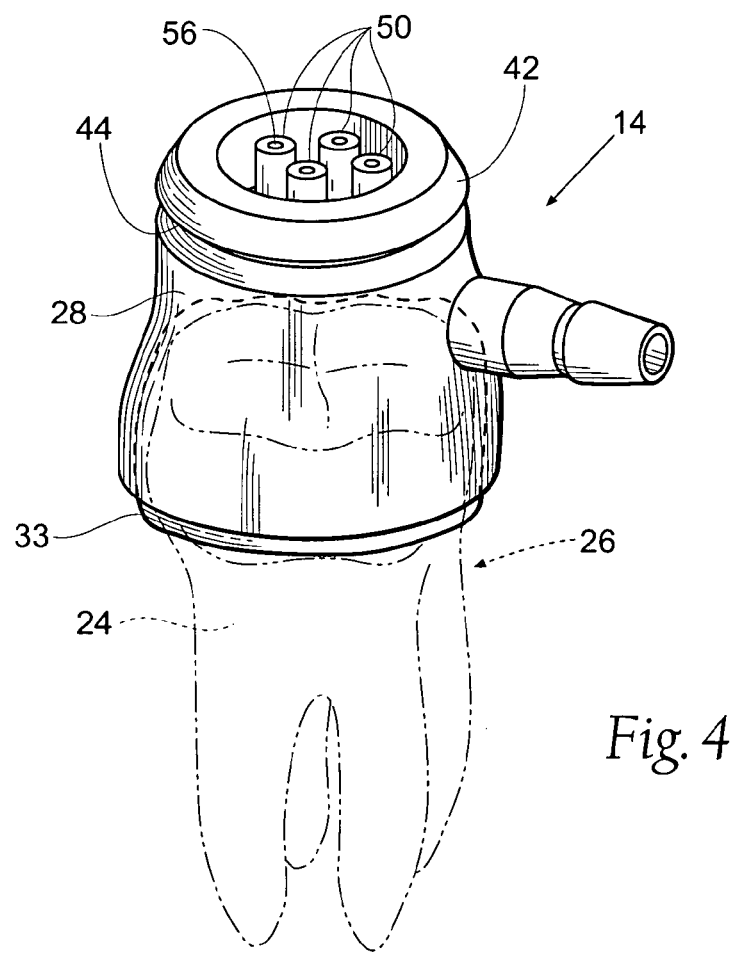
FIG. 4 is a perspective view of the base shown in FIG. 3 placed on the crown of an instrumented tooth.

As best illustrated in FIG. 2, the needle 18 includes a shaft 48 and a head or upper manifold reservoir 50 coupled to the proximal end of the shaft 48. The shaft 48 defines a lumen 52 and is formed from a durable, flexible material that retains its memory when inserted into a non-linear passage (i.e., a root canal 34), e.g., nickel-titanium, so as to minimize kinking or breaking. The material may also be a cutable material, e.g., stainless steel or polyamide-coated stainless steel. The needle head 50 includes an opening or solution input aperture 56 that is in fluid communication with the needle lumen 52. The head 50 can be made of any suitable biocompatible material.

Figure 6A:
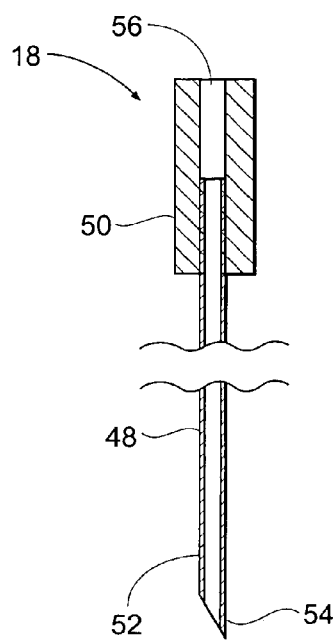
FIG. 6A is a fragmented view of an alternative embodiment of a needle in which the needle has a beveled distal end.
Figure 6B:
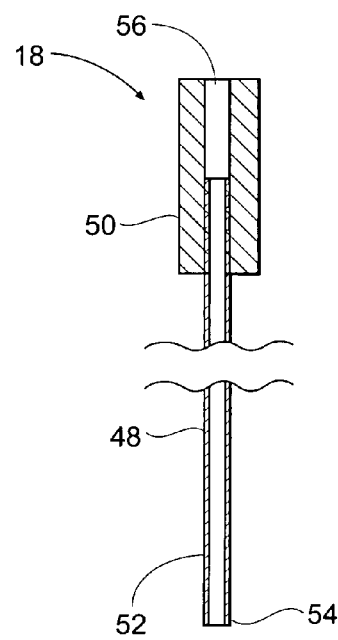
FIG. 6B is a fragmented view of an alternative embodiment of a needle in which the needle has a blunt distal end.
Figure 6C:
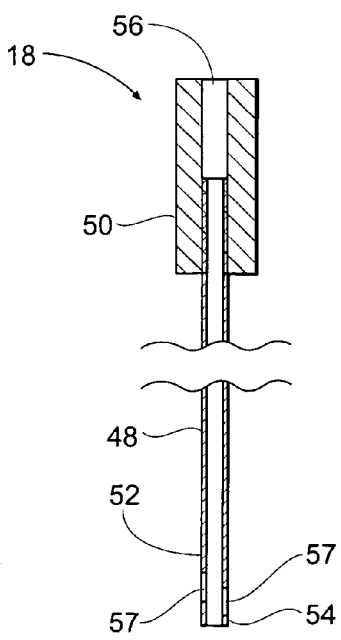
FIG. 6C is a fragmented view of an alternative embodiment of a needle in which the needle has a blunt distal end and includes side vents.

In the embodiment illustrated in FIGS. 2–5, the distal end 54 of the shaft 48 is scived and tapered to withstand vacuum pressure during the evacuation cycle without plugging. In alternative embodiments, the distal end 54 is beveled, as shown in FIG. 6A, blunt, as shown in FIG. 6B, or blunt with side vents 57, as shown in FIG. 6C. It is to be understood that the number and configuration of vents 57 can vary as desired.

The distal end 54 of the needle 18 is passed through a selected opening 40 in the screen 38 and through the bottom 30 of the base 14 into a pulp canal 34 that has previously been instrumented. The length of the needle shaft 48 can be selected to place the distal end 54 of the needle 18 at a desired depth. Desirably, the needle 18 length is selected so that the distal end 54 of the needle 18 extends deep within the pulp canal 34.

A conventional long needle gauge having incremented markings may be provided to the practitioner to measure the depth of the root canal 34 and cut or trim the needle 18 to the desired length (not shown).

The practitioner can chose from the plurality of openings 40 to place the needle shaft 48 at or near the center of the selected pulp canal 34 so as to easily position the distal end 54 of the needle 18 deep within the pulp canal 34. The screen 38 therefore allows the system 10 to accommodate individual anatomy and tooth 26 structure.

The head portion 50 is sized and configured to rest on the screen 38 and to prevent passage of the head 50 through the opening 40. Additional needles 18 may be inserted as needed into other instrumented pulp canals 34 within the tooth 26.

Figure 7:
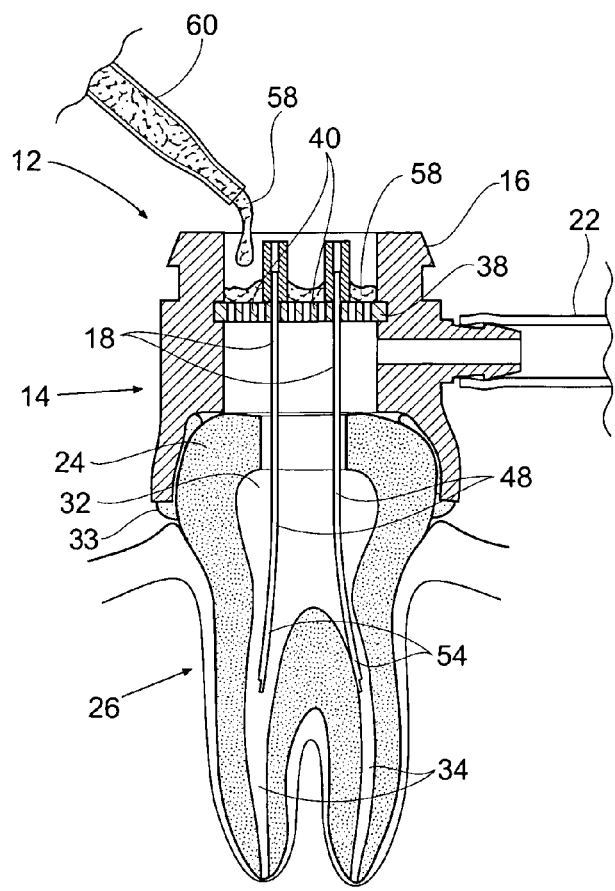
FIG. 7 is a view similar to FIG. 5 and illustrating placement of a sealing composition over the unused openings in the screen.

As illustrated in FIG. 7, unused openings 40 in the screen 38 are then preferably closed or sealed by placing a sealing composition 58 over the remaining openings 40 in the screen 38. The sealing composition 58 is a fluent material that converts to a non-fluent material upon exposure to air and/or light. Desirably, the sealing composition 58 is of sufficient viscosity to prevent significant passage of the composition 58 through the openings 40 while the composition 58 sets.

The composition 58 may be delivered in any suitable manner. In the illustrated embodiment, the composition 58 is delivered by a dropper 60 or other suitable pipetting device. Alternatively, the composition 58 may be delivered by brushing the material over the screen 38 with a brush (not shown).

The composition 58 is selected so as to provide a satisfactory seal with minimal setting time. The composition 58 may be a resin or a light curable material.

The cap 16 is ladle-shaped or otherwise sized and configured to fit over the base member 14 and couple with the annular ridge 42 of the base 14 in a snug-fit engagement. The cap 16 may be semi-flexible to apply additional pressure on the base skirt 28 around the tooth 26 to further seal the tooth 26.

Figure 8:
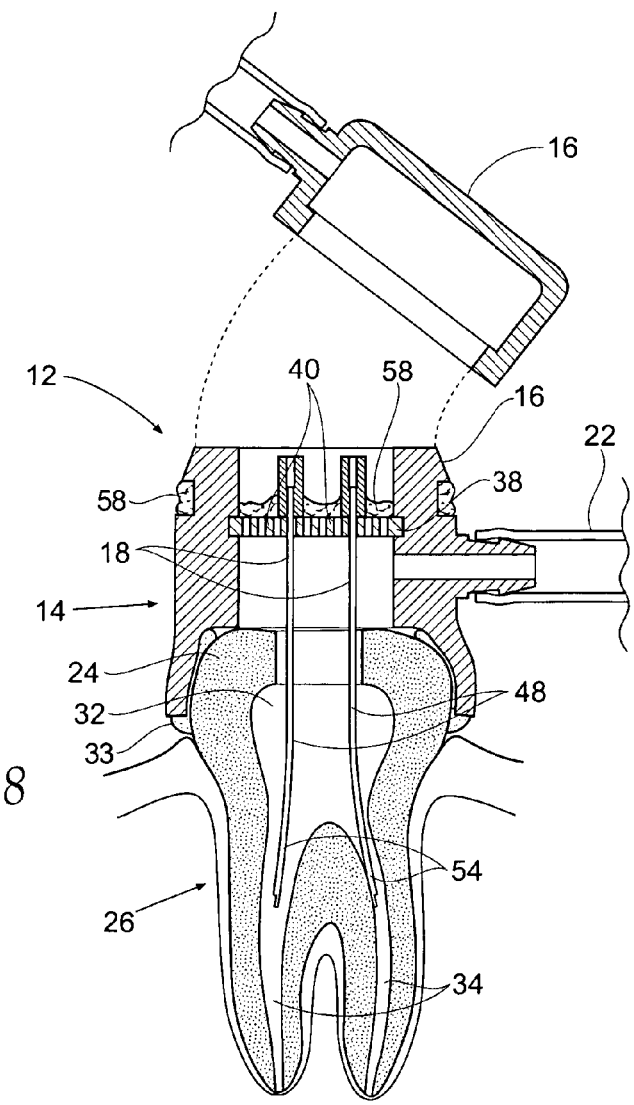
FIG. 8 is a view similar to FIG. 7 and illustrating the placement of sealing composition along the annular ridge of the base to secure the cap.

As shown in FIG. 8, the cap 16 may be further sealed onto the base 14, e.g., by placing a small amount of light curable sealing compound 58 (our other suitable biocompatible sealing material) around the annular ridge 42 before securing the cap 16 onto the base.

The cap 16 includes an inner surface 62 that, together with the screen 38, defines an inlet chamber 64. Setting or gelling of the sealing composition 58 plugs the openings 40 in the screen 38 to form a barrier defining discrete inlet and outlet chambers 64 and 46 and preventing fluid communication between the chambers 64 and 46.

The cap 16 can be made of any suitable biocompatible material.

The distal end 54 of the needle lumen 52 is in fluid communication with the outlet chamber 46. The inlet chamber 64 is in fluid communication with each needle lumen 52 through aperture 56 in the needle head 50, as previously noted.

The manifold 12 is desirably formed of disposable materials and adapted for single use. The needles 18 may be formed of materials which may be sterilized, e.g., by ethylene oxide, for reuse.

Figure 9:
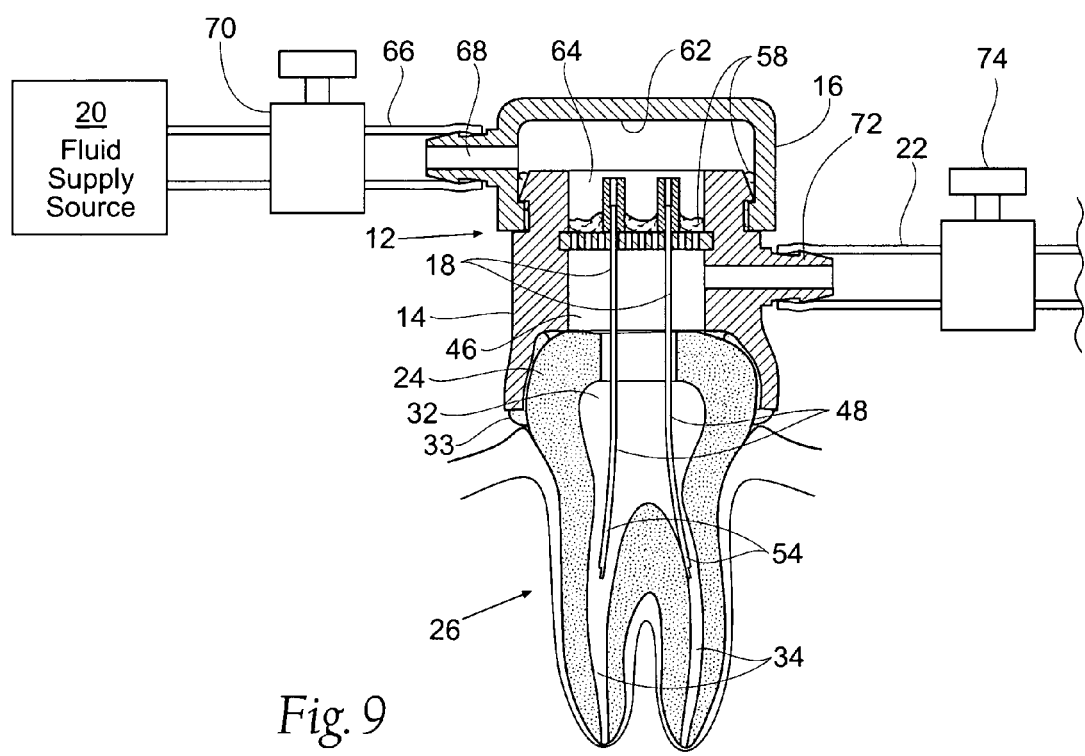
FIG. 9 is a view similar to 8 and illustrating placement of the cap on the base.

Referring now to FIG. 9, the inlet chamber 64 is coupled to a low pressure fluid supply source 20 by inlet tubing 66 at an inlet port 68 in the cap 16. The fluid supply source 20 provides treatment solution, irrigation solution, or another desired solution (S). An inlet flow control valve 70 may be coupled to the inlet tubing 66 to permit regulation of the flow of the solution (S) into the inlet chamber 64.

The outlet chamber 46 is coupled to the evacuation tubing 22 at an outlet port 72 in the base 14. The evacuation tubing 22 is coupled to a vacuum source as is known in the art (not shown). An evacuation flow control valve 74 may be coupled to the evacuation tubing 22 to permit regulation of the flow of spent solution (S) from the outlet chamber 46.

Figure 10:
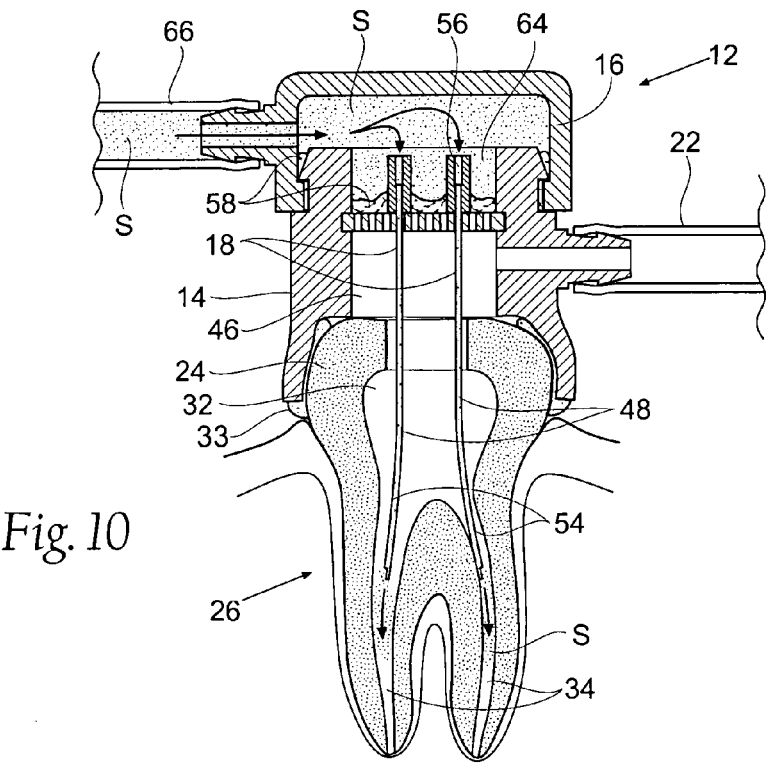
FIG. 10 is a view similar to FIG. 9 and illustrating the flow of fluid from the inlet chamber through the needle and delivery of fluid from the distal end of the needle into the pulp canals.

As represented by arrows in FIG. 10, the solution (S) is drawn into the inlet chamber 64 and subsequently through the needle 18 by way of the aperture 56 and delivered through the distal end 54 of the needle 18 into the pulp canal 34 to flood the pulp chamber 32 and pulp canals 34 with the solution. That is, the solution (S) is delivered under pressure directly to the bottom of the fluid reservoir formed by the pulp chamber 32 and pulp canals 34.

Figure 11:
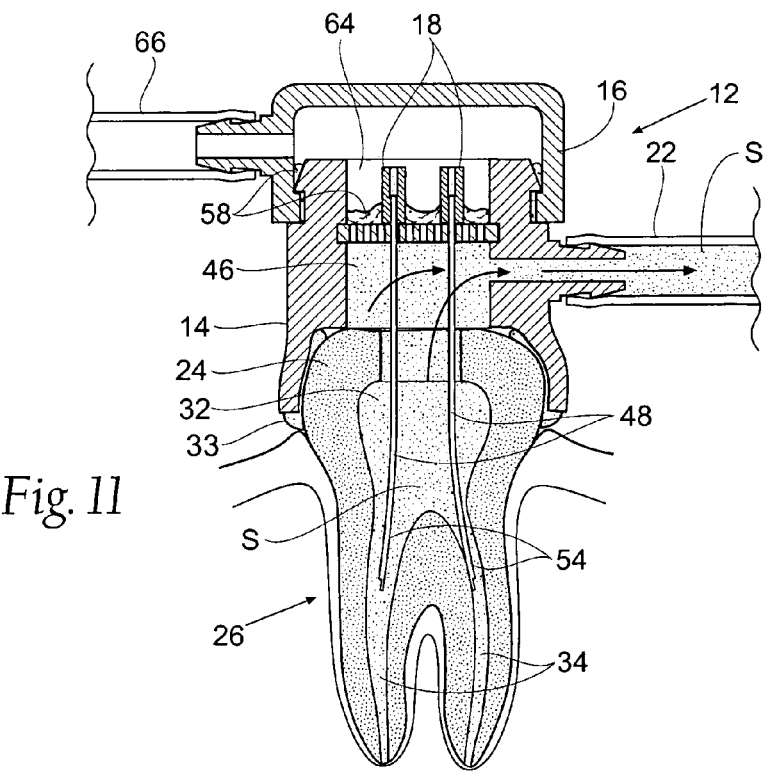
FIG. 11 is a view similar to FIG. 10 and illustrating the evacuation of spent fluid from the pulp chamber and pulp canals through the evacuation chamber.
Figure 12:
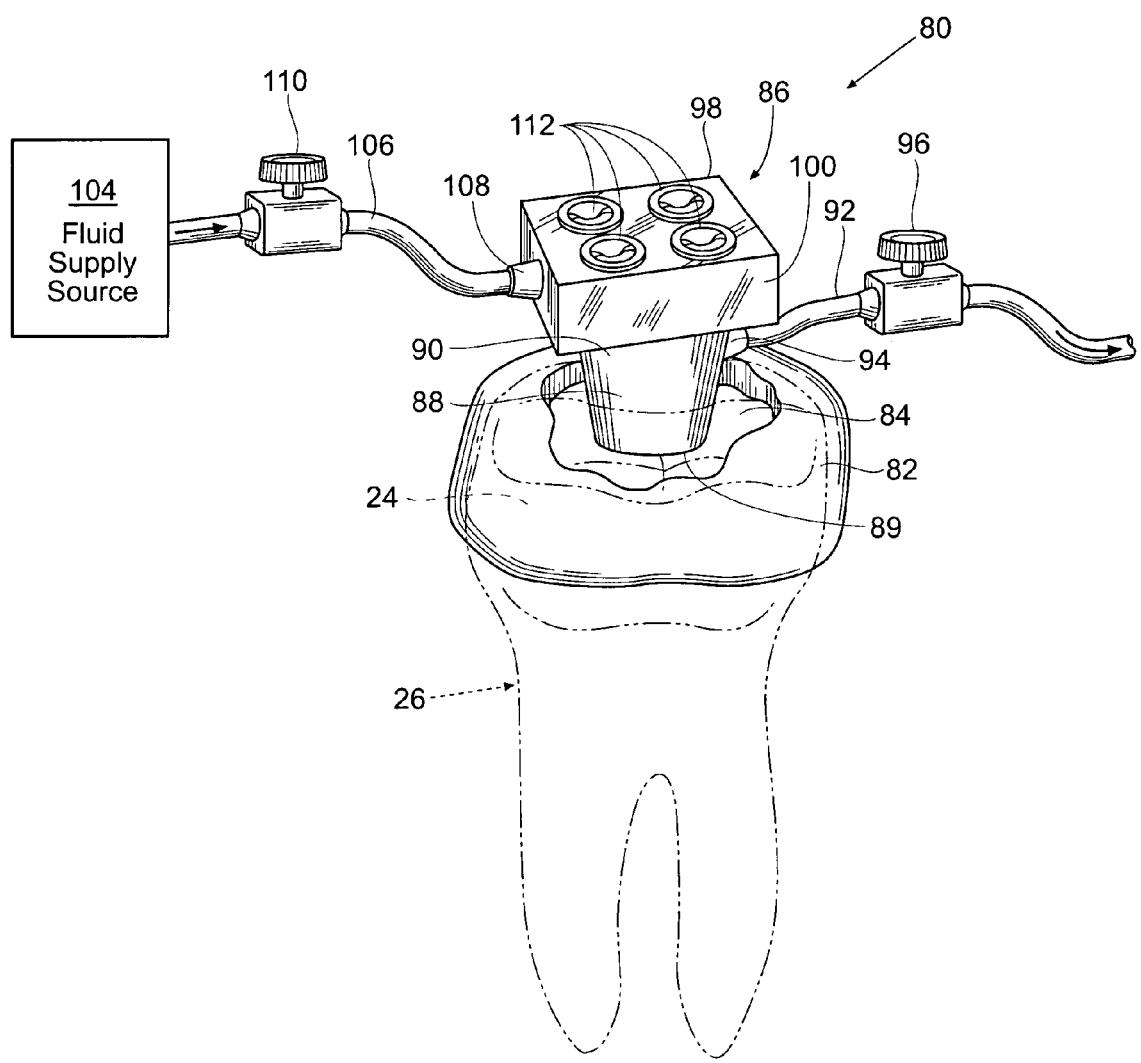
FIG. 12 is a perspective view of an alternative system for treating tooth root canals.
Figure 13:
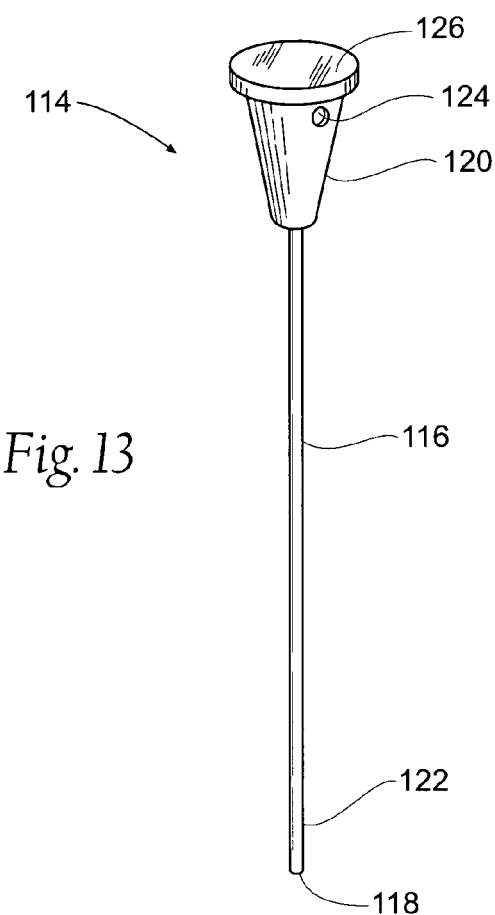
FIG. 13 is a perspective view of a needle for use with the system shown in FIG. 12.
Figure 14:
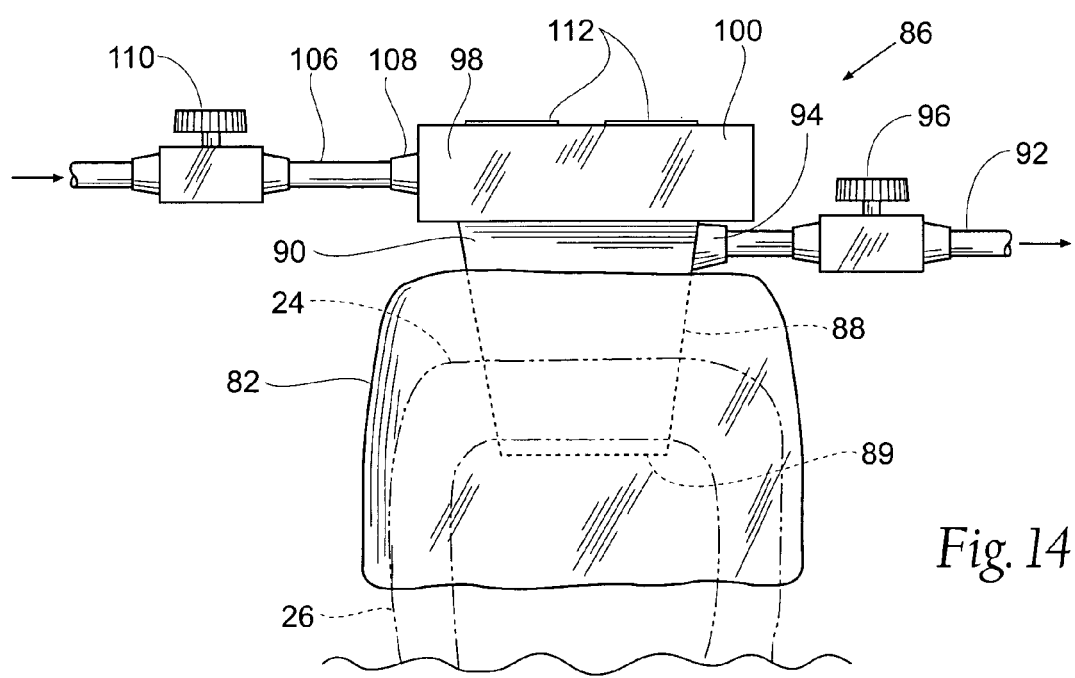
FIG. 14 is a front plan view of the system shown in FIG. 12 in place within an instrumented tooth.
Figure 15:
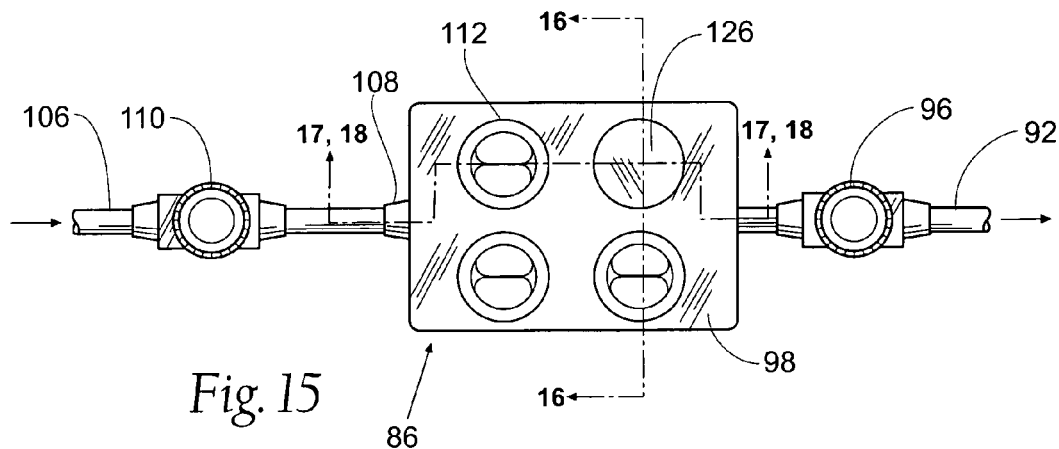
FIG. 15 is a top plan view of the system shown in FIG. 12.
Figure 16:
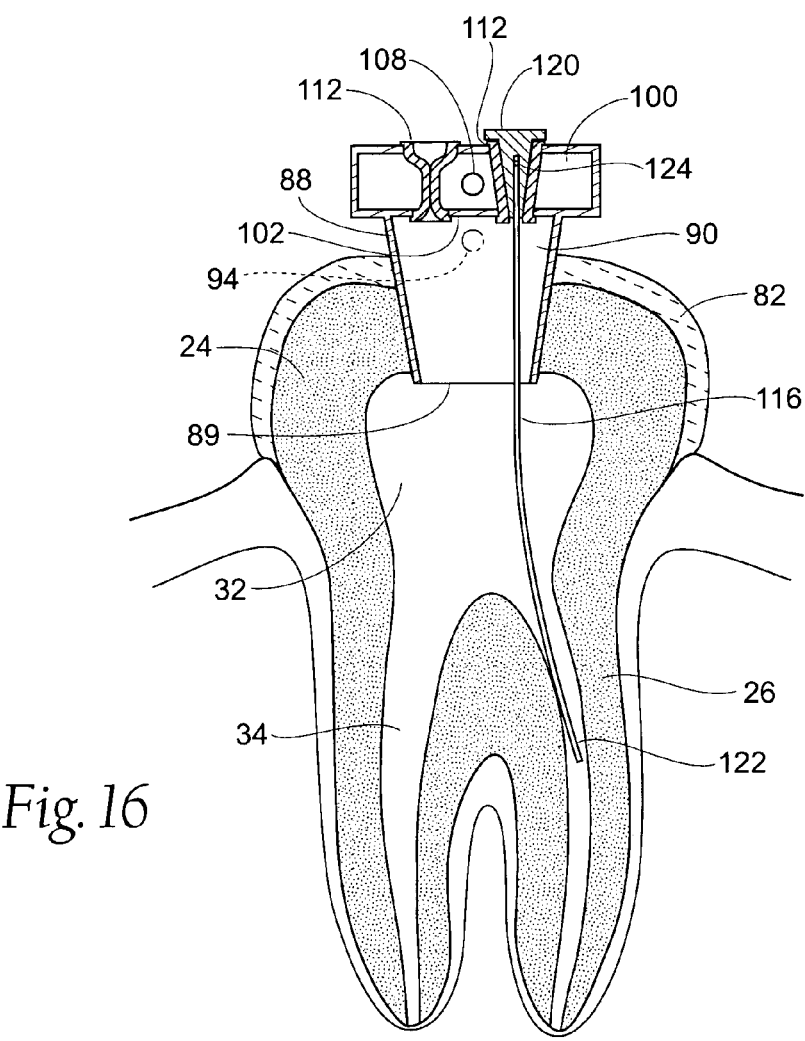
FIG. 16 is a sectional view of the system in place within an instrumented tooth taken along line 16—16 of FIG. 15.

The vacuum pressure created by the vacuum source draws the spent solution (S) out of the pulp canals 34 and pulp chamber 32 through the evacuation chamber 46 and the spent solution (S) exits the manifold 12 through the evacuation tubing 22, as represented by arrows in FIG. 11. Because the vacuum source is the path of least resistance for the solution (S), leakage is minimal. The system 12 assures essentially complete drainage of the spent solution (S) from the fluid reservoir during each cycle.

It is desirable that the irrigation and evacuation pressures are approximately balanced or that the evacuation pressure is slightly greater than the irrigation pressure to provide a net negative pressure within the manifold 12. The balanced or slight negative pressure serves to help retain the manifold 12 on the tooth 26 and helps prevent caustic chemicals from passing from the root canals 34 into the sinus cavity.

In use, the tooth 26 is instrumented by conventional techniques as is known in the art. The practitioner then places the base 14 on the instrumented tooth 26 to seal the tooth 26 and the screen 38 is placed on the base 14. A desired number of needles 18 are passed through selected openings 40 in the screen 38 and into the instrumented pulp canals 34. The practitioner then applies sealing composition 58 to the screen 38 and allows the composition 58 to set, thereby creating a floor or barrier between the inlet and outlet chambers 64 and 46.

The cap 16 is coupled to the base 14 to close the manifold 12. The base 14 (and thus evacuation chamber 46) is coupled to the evacuation tubing 22 and vacuum source. The cap 16 (and thus inlet chamber 64) is coupled to the inlet tubing 66 and a treatment solution supply source 20.

The practitioner then programs the system 10 for the desired parameters, selecting cycle time, number of cycles, and volume of solution (S) to be delivered. In preparing multiple teeth 26, each manifold 12 may be programmed separately.

The system 10 is activated to cycle the treatment solution (S) through the pulp chamber 32 and pulp canals 34. Upon completion of the treatment program, the treatment solution supply source 20 is disconnected and the inlet tubing 66 is coupled to an irrigation solution supply source 20.

The system 10 is again programmed for the desired cycle parameters and the system 10 activated to cycle the irrigation solution (S) through the pulp chamber 32 and pulp canals 34. Upon completion of the irrigation program, the needles 18 and the manifold 12 are removed. The endodontic procedure may then be completed as necessary, e.g., by introducing filling material into the prepared pulp canals 34 (not shown).

II. Alternative Embodiment

FIGS. 12 to 18 detail an alternative embodiment of an automated system 80 for delivering a solution (S) to a pulp chamber 32 and pulp canals 34 during endodontic therapy.

A flexible skirt 82 is adapted to be placed over the crown 24 of an instrumented tooth 26. The skirt 82 has an opening 84 to accommodate the passage of a tooth manifold 86. Together with the manifold 86, the skirt 82 acts to vacuum seal the tooth 26 to prevent leakage of solution (S) into the patient's mouth. In the illustrated embodiment, the skirt 82 extends 360 degrees around the tooth 26. However, the skirt 82 need not extend 360 degrees around the tooth 26 to assure retention of the skirt 82 on the crown 24 and sealing of the tooth 26.

The skirt 82 can be made of any suitable biocompatible material. The skirt 82 is desirably adapted to be disposable after a single use.

The manifold 86 includes a base portion 88 having an open bottom 89 and defining an outlet or evacuation chamber 90. The base 88 passes through the opening 84 in the skirt 82 and is desirably flanged to rest on the crown 24 of an instrumented tooth 26. The evacuation chamber 90 is in fluid communication with the pulp chamber 32 and pulp canals 34. The outlet chamber 90 is coupled to an evacuation tubing 92 at an outlet port 94 in the base 88. The evacuation tubing 92 is coupled to a vacuum source as in known in the art (not shown). An evacuation flow control valve 96 may be coupled to the evacuation tubing 92 to permit regulation of the flow of the solution (S) from the outlet chamber 90.

The manifold 86 includes an upper or cap portion 98 defining an inlet chamber or reservoir 100. A partitioning wall 102 partitions the cap 98 from the base 88 to prevent communication between the inlet and outlet chambers 100 and 90. The inlet chamber 100 is coupled to a low-pressure fluid supply source 104 by an inlet tubing 106 at an inlet port 108 connector on the cap 98. An inlet flow control valve 110 may be coupled to the inlet tubing 106 to permit regulation of the flow of the solution (S) into the inlet chamber 100.

The cap portion 98 includes a plurality of valve apertures 112, e.g., duck bill apertures. In the closed position, the valves 112 prevent communication between the base 88 and the cap 98, i.e., between the outlet and the inlet chambers 90 and 100. In a preferred embodiment, each valve 112 is normally biased in the closed position. In the open position, the valves 112 permit communication between the base 88 and the cap 98, i.e., between the outlet and the inlet chambers 90 and 100.

The manifold 86 can be made of any suitable biocompatible material. The manifold 86 is desirably adapted to be disposable after a single use.

In a preferred embodiment, each valve aperture 112 is adapted to receive a needle 114 for placement of the needle 114 deep within a selected pulp canal 34 (which has been previously instrumented). The needle 114 permits pressured release of solution (S) and evacuation of the spent solution (S) from deep within the pulp canals 34. It is contemplated that the number and placement of the valve apertures 112 may be varied to accommodate a particular tooth 26 structure and individual anatomy.

Figure 18:
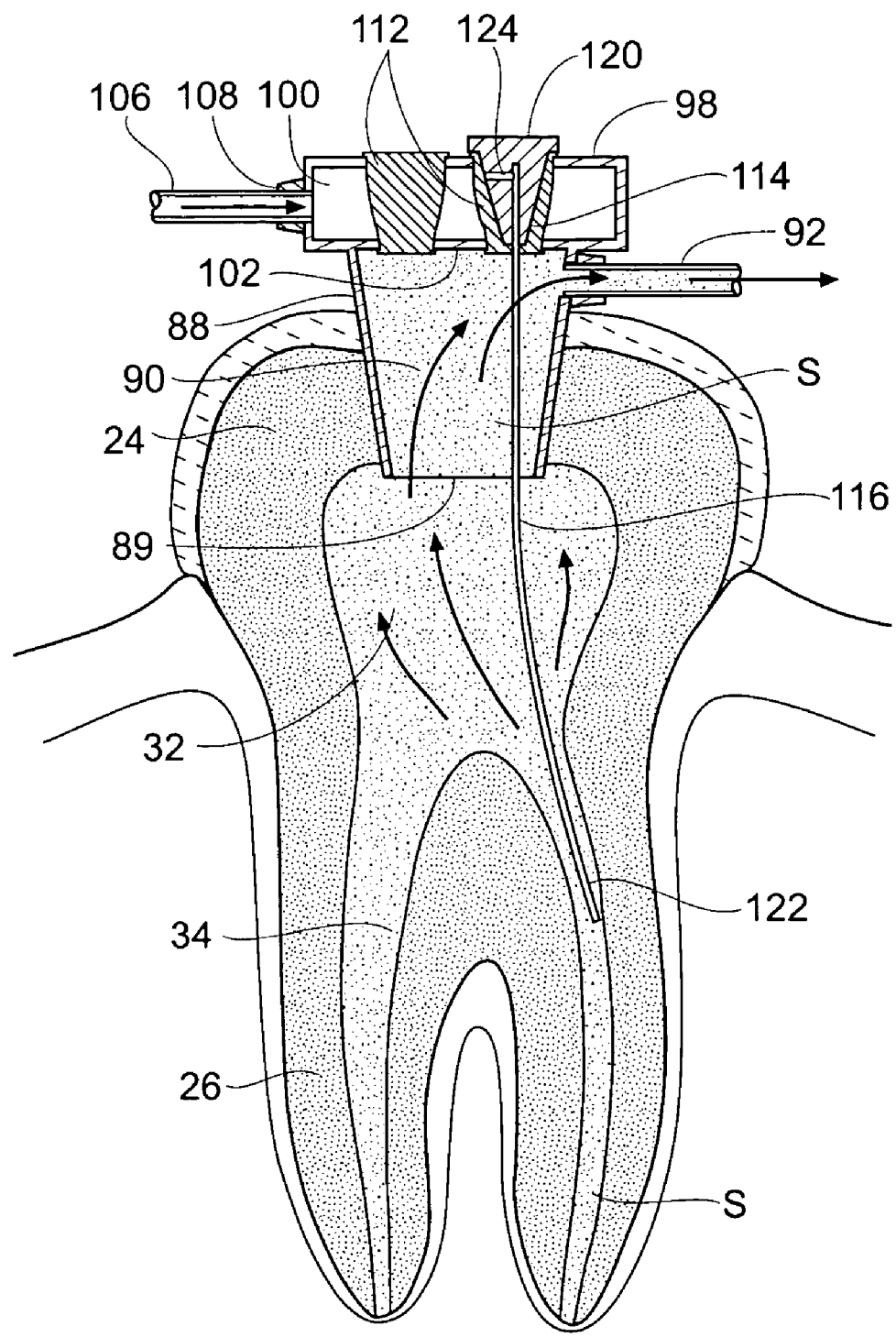
FIG. 18 is a view similar to FIG. 17 and illustrating the evacuation of spent fluid from the pulp chamber and pulp canals through the evacuation chamber

As best seen in FIG. 18, the needle 114 includes a flexible shaft 116 defining a lumen 118 and an upper manifold reservoir or head 120 coupled to the shaft 116. The needle 114 is similar to the embodiment shown in FIGS. 1–11. The shaft 116 is preferably formed from a durable, flexible material, e.g., nickel-titanium, so as to minimize kinking or breaking. In the illustrated embodiment, the distal end 122 of the shaft 116 is blunt (see also FIG. 6B). In alternative embodiments, the distal end 122 is scived and tapered (see, e.g., FIGS. 2 and 3), blunt with side vents 57 (see, e.g., FIG. 6C) or beveled (see, e.g., FIG. 6A).

The head 120 includes an opening or solution input aperture 124 that is in fluid communication with the needle lumen 118. The head 120 can be made of any suitable biocompatible material. The head 120 is sized and configured for placement within a valve aperture 112 to move the valve 112 from the closed to the open position. The needle head 120 is desirably of a complementary geometry to the valve aperture 112 to provide a snug fig engagement within the valve. The snug fit engagement secures the needle 114 within the manifold 86 while maintaining discretion between the inlet and outlet chambers 100 and 90. In the illustrated embodiment, the head 120 is a circular hub permitting rotation of the needle 114 within the valve 112 to enable proper alignment of the needle 114.

Desirably, the head 120 includes a sealing member 126. The sealing member 126 serves to minimize leakage of solution (S) from the needle head 120 and/or the inlet chamber 100. The sealing member 126 may be integral with the head 120 or molded as a separate piece for selective, removable engagement with the head 120.

Figure 17:
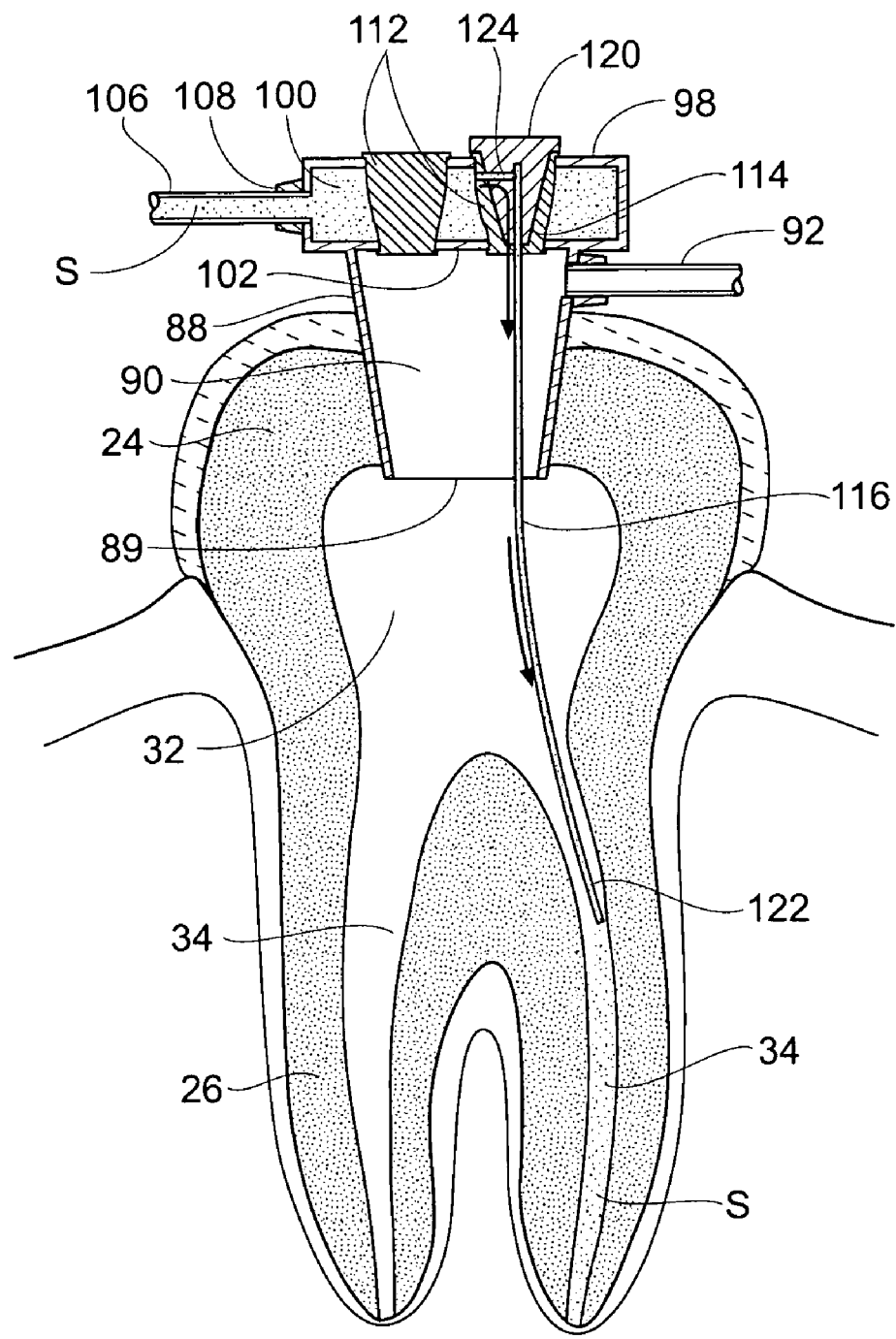
FIG. 17 is a sectional view taken along line 17, 18–17, 18 of FIG. 15, turned 90° relative to FIG. 16 and illustrating the flow of fluid from the inlet chamber through the needle and delivery of fluid from the distal end of the needle into the pulp canals.

As represented by arrows in FIG. 17, the solution (S) is drawn into the inlet chamber 100 and thus through the needle 114 by way of the aperture 124 and lumen 118 for pressurized release of the solution (S) through the distal end 122 of the needle 114 into the pulp canal 34 to flood the pulp chamber 32 and pulp canal 34 with the solution (S). The solution (S) is thereby delivered to the bottom of the fluid reservoir defined by the pulp chamber 32 and pulp canals 34.

The vacuum pressure created by the vacuum source draws the spent solution (S) out from pulp canals 34, pulp chamber 32 and evacuation chamber 90 through the evacuation tubing 92, as represented by arrows in FIG. 18.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A tooth root canal treatment system comprising
a manifold having a base member sized and configured to rest on a crown of a tooth and a top member sized and configured to couple with the base member to define an inlet chamber and an outlet chamber,
means for preventing fluid communication between the inlet chamber and the outlet chamber,
an opening between the inlet and outlet chambers,
a needle having a proximal end and a distal end, the distal end of the needle sized and configured for passage through the opening between the inlet and outlet chambers and extending distally beyond the base member and in fluid communication with the outlet chamber, the proximal end of the needle including an opening in fluid communication with the inlet chamber,
a fluid supply source coupled to the inlet chamber, and
a draining mechanism coupled to the outlet chamber.

2. A tooth root canal treatment system
a manifold having a base member sized and configured to rest on a crown of a tooth and a top member sized and configured to couple with the base member to define an inlet chamber and an outlet chamber,
means for preventing fluid communication between the inlet chamber and the outlet chamber,
an opening between the inlet and outlet chambers,
a needle having a proximal end and a distal end, the distal end of the needle sized and configured for passage through the opening between the inlet and outlet chambers and extending distally beyond the base member and in fluid communication with the outlet chamber, the proximal end of the needle including an opening in fluid communication with the inlet chamber,
means for delivering a fluid source to the inlet chamber, and
means for draining the outlet chamber.

3. A tooth root canal treatment system as in claim 1 or 2 wherein the needle includes a flexible shaft.

4. A tooth root canal treatment system as in claim 1 or 2 wherein the opening between the inlet and outlet chambers is a perforation.

5. A tooth root canal treatment system as in claim 1 or 2 wherein the opening between the inlet and outlet chambers comprises a valve.

6. A tooth root canal treatment system as in claim 5 wherein the valve is a duck bill valve.

7. A tooth root canal treatment system as in claim 1 or 2 wherein the fluid is a treatment solution.

8. A tooth root canal treatment system as in claim 1 or 2 wherein the fluid is an irrigation solution.

9. A tooth root canal treatment system as in claim 1 or 2, further comprising
means for maintaining a net negative pressure within the manifold.

10. A tooth root canal treatment system comprising
a manifold having a base member sized and configured to rest on a crown of a tooth and a top member sized and configured to couple with the base member to define an inlet chamber and an outlet chamber,
means for preventing fluid communication between the inlet chamber and the outlet chamber,
a fluid supply source coupled to the inlet chamber,
a draining mechanism coupled to the outlet chamber, and
means for maintaining a net negative pressure within the manifold.

11. A method of treating a tooth root canal comprising the steps of
(a) providing a needle having a proximal end and a distal end,
(b) placing a base on a crown of an instrumented tooth,
(c) passing the distal end of the needle through an opening in the base and through a pulp chamber and a pulp canal of the tooth,
(d) placing a cap on the base to form a tooth manifold, the tooth manifold having an inlet chamber and an outlet chamber, the proximal end of the needle communicating with the inlet chamber and the distal end of the needle communicating with the outlet chamber,
(e) coupling the inlet chamber to a fluid source,
(f) coupling the outlet chamber to a draining mechanism,
(g) drawing the fluid through the inlet chamber into the pulp chamber and pulp canal, and
(h) evacuating the fluid from the pulp chamber and the pulp canal through the outlet chamber.

12. A method as in claim 11, further comprising
repeating steps (g) and (h).

13. A method as in claim 11, further comprising
maintaining a net negative pressure within the manifold.

14. A method of treating a tooth root canal comprising the steps of
(a) placing a base on a crown of an instrumented tooth,
(b) placing a cap on the base to form a tooth manifold, the tooth manifold having an inlet chamber and an outlet chamber, the manifold including means for preventing fluid communication between the inlet and outlet chambers,
(c) coupling the inlet chamber to a fluid source,
(d) coupling the outlet chamber to a draining mechanism,
(e) drawing the fluid through the inlet chamber into the pulp chamber and pulp canal, and
(f) evacuating the fluid from the pulp chamber and the pulp canal through the outlet chamber, and
(g) maintaining a net negative pressure within the manifold during while drawing the fluid and evacuating the fluid.

15. An automated system for treating a tooth root canal having a pulp chamber and pulp canal defining a fluid reservoir, the system comprising
- a tooth manifold having an inlet chamber and an outlet chamber, the inlet chamber being coupleable to a fluid supply source and the outlet chamber being coupleable to an evacuation source,
- means for directing fluid from the inlet chamber directly into the pulp canal, bypassing the pulp chamber, and
- means for evacuating the fluid from the fluid reservoir through the evacuation chamber.

16. A system as in claim 15, further comprising
- means for maintaining a net negative pressure within the manifold while directing fluid from the inlet chamber into the pulp canal and while evacuating the fluid from the fluid reservoir.

* * * * *

UNITED STATES PATENT AND TRADEMARK OFFICE
CERTIFICATE OF CORRECTION

PATENT NO. : 6,971,878 B2  
DATED : December 6, 2005  
INVENTOR(S) : Gary J. Pond It is certified that error appears in the above-identified patent and that said Letters Patent is hereby corrected as shown below:

<u>Column 10,</u>
Lines 65-66, after "manifold" delete "during".

Signed and Sealed this

Twenty-first Day of March, 2006

JON W. DUDAS
*Director of the United States Patent and Trademark Office*